(12) United States Patent
Alkoby et al.

(10) Patent No.: US 12,721,923 B2
(45) Date of Patent: Sep. 1, 2026

(54) AIR AND SURFACE TREATMENT SYSTEM

(71) Applicant: BIO PHARMAX GROUP (1996) LTD., Herzeliya Pituach (IL)

(72) Inventors: Asher Desire Alkoby, Ramat Hasharon (IL); Max Kozman, Petah Tikva (IL); Sarel Chaim Chen Tov, Kfar Sirkin (IL)

(73) Assignee: BIO PHARMAX GROUP (1996) LTD, Herzeliya Pituach (IL)

( * ) Notice: Subject to any disclaimer, the term of this patent is extended or adjusted under 35 U.S.C. 154(b) by 657 days.

(21) Appl. No.: 18/009,059

(22) PCT Filed: Jun. 9, 2021

(86) PCT No.: PCT/IL2021/050696
§ 371 (c)(1),
(2) Date: Dec. 8, 2022

(87) PCT Pub. No.: WO2021/250671
PCT Pub. Date: Dec. 16, 2021

(65) Prior Publication Data

US 2023/0248874 A1 Aug. 10, 2023

Related U.S. Application Data

(60) Provisional application No. 63/036,684, filed on Jun. 9, 2020.

(51) Int. Cl.
*A61L 2/00* (2006.01)
*A61L 2/10* (2006.01)
(Continued)

(52) U.S. Cl.
CPC ................ *A61L 9/145* (2013.01); *A61L 2/10* (2013.01); *A61L 2/18* (2013.01); *A61L 2/26* (2013.01);
(Continued)

(58) Field of Classification Search
CPC ........... A61L 9/14; A61L 9/18; A61L 2209/13
USPC ........................................ 422/5, 24, 123, 306
See application file for complete search history.

(56) References Cited

U.S. PATENT DOCUMENTS 6,363,734 B1 4/2002 Aoyagi et al.
8,318,084 B2 11/2012 Johnson et al.
2008/0112845 A1 * 5/2008 Dunn ..................... F24F 8/167 362/221

FOREIGN PATENT DOCUMENTS

CN 103894061 7/2014
CN 205655419 10/2016
(Continued)

OTHER PUBLICATIONS

Machine English Translation of the Description Section of CN 205655419 U.*
(Continued)

*Primary Examiner* — Monzer R Chorbaji
(74) *Attorney, Agent, or Firm* — A.C. Entis-IP Ltd; Allan C. Entis

(57) ABSTRACT

An air treatment system comprising: an air purification assembly comprising one or more air purification modules and configured to, in an upstream to downstream order, take in air, produce purified air by conveying the air to traverse the one or more air purification modules, and expel the purified air, and an aerosol source configured to release a conditioning liquid in aerosol form into the purified air. Optionally, the conditioning liquid comprises a predetermined concentration of nonpathogenic micro-organisms. Optionally, one or more air purification modules comprises, in an upstream to downstream order, a HEPA or ULPA filter, a UVC irradiation unit, and an activated carbon filter.

6 Claims, 5 Drawing Sheets

(51) Int. Cl.

| | |
|---|---|
| ***A61L 2/18*** | (2006.01) |
| ***A61L 2/26*** | (2006.01) |
| ***A61L 9/00*** | (2006.01) |
| ***A61L 9/14*** | (2006.01) |
| ***A61L 9/20*** | (2006.01) |

(52) U.S. Cl.
CPC ............. *A61L 9/20* (2013.01); *A61L 2202/11* (2013.01); *A61L 2202/15* (2013.01); *A61L 2209/14* (2013.01)

(56) References Cited

FOREIGN PATENT DOCUMENTS

| | | | |
|---|---|---|---|
| CN | 205655419 U | * 10/2016 | .............. F24F 11/00 |
| CN | 201811043403 | 12/2018 | |
| CN | 210114903 | 2/2020 | |
| KR | 20120038300 | 10/2013 | |
| WO | 2006076334 | 7/2006 | |
| WO | 2012068131 | 5/2012 | |
| WO | 2019046648 | 3/2019 | |

OTHER PUBLICATIONS

European Partial Search Report dated May 17, 2024, Application No. 21821411.2 filed Dec. 9, 2022.

European Extended Search Report dated Aug. 7, 2024, Application No. 21821411.2 filed Dec. 9, 2022.

International Search Report dated Oct. 5, 2021, in corresponspond-ing international application PCT/IL2021/050696 filed Jun. 9, 2021.

Israeli Office Action dated Mar. 27, 2025 for Application No. 298963 filed Dec. 8, 2022.

* cited by examiner

Chart 1

| | UVC+ Ionizer system | | | ESP-based system | | | Comb. system | UVC + Carbon |
|---|---|---|---|---|---|---|---|---|
| | Option A | Option B | Option C | Option D | Option E | Option F | Option G | Option H |
| **G2-E12 Pre Filter** | + | + | + | + | + | + | + | + |
| **HEPA or ULPA Main Filter** | | + | + | | + | + | + | +/- |
| **Blower** | + | + | + | + | + | + | + | + |
| **UVC** | + | + | + | | | + | + | + |
| **ESP** | | | | + | + | + | + | |
| **Carbon Filter** | | | + | + | + | + | + | + |
| **$O_2$ Ionizer** | + | + | + | | | | + | |
| **Aerosol source** | +/- | +/- | +/- | +/- | +/- | +/- | +/- | +/- |

FIG. 1

AIR AND SURFACE TREATMENT SYSTEM

RELATED APPLICATIONS

The present application is a U.S. National Phase of PCT Application PCT/IL2021/050696 filed on Jun. 9, 2021, claiming benefit under 35 U.S.C. 119(e) of U.S. Provisional Application 63/036,684 filed Jun. 9, 2020, the disclosures of which are incorporated herein by reference.

BACKGROUND

Air inside indoor spaces may contain various airborne bioactive agents (ABAs) that are harmful to people. By way of example, a viral infection can spread among a population through virus-containing airborne particles (VCAPs) that begin as aerosolized bioliquids arising from, by way of example, breathing, speaking, sneezing, and coughing. The VCAPs, especially smaller ones, can remain airborne for an extended period of time, either as aerosols or desiccated particles. Moreover, the virus comprised in the VCAPs can remain viable for a sufficient duration within the VCAPs so that the VCAPs can serve as a vector for transmission of the virus to others. A VCAP comprising viable virus that is able to infect a hew host may be referred to herein as an "active VCAP" or "aVCAP".

Other examples of ABAs include molds, bacteria, allergens, and volatile organic compounds.

Air filtration systems configured to reduce or remove ABAs are typically specialized systems for limited use in hospitals and are cost-prohibitive for wider use in commercial and residential settings. Other potential solutions, such as short-wavelength ultraviolet (UVC) irradiation that is known to neutralize the bioactivity of ABAs can only be deployed intermittently when a room is unoccupied. There is need for a cost-effective, high performance system capable of reducing ABAs in a room. In addition, given the recent coronavirus pandemic, there is a need for a cost-effective, high performance system compatible with HVAC systems capable of reducing active VCAP load.

SUMMARY

An aspect of an embodiment of the disclosure relates to a system and method for treating air collected from residential and office settings to efficiently remove or reduce ABAs present in the air and surfaces of a room by passing the air through a combination of filtration and irradiation treatments, as well.

For convenience of presentation, the system in accordance with an embodiment of the disclosure may be referred to as an "ABA reduction system", An ABA reduction system may comprise an air conveyer such as a fan, which may be referred to as a "blower", and be configured to propel air to traverse a combination of two or more air treatment units selected from the group consisting of: at least one particulate filtration unit; an electrostatic precipitation (ESP) unit; a UVC irradiation unit; an activated carbon filtration unit; an $O_2$ ionization unit, and an aerosol source.

A particulate filtration unit is configured to allow passage of air while blocking passage of airborne particles. Typically, particulate filtration units are graded by the size of particles that are blocked or allowed passage. Examples of particulate filtration units include high-efficiency particulate absorbing (HEPA) filter units, Ultra-Low Particulate Air (ULPA) filter units, and various types of pre-filters.

In ESP-based air filtration using an ESP unit, an air stream flows through thin electrodes, and then through a collection of conductive surfaces, in which a voltage is applied between the thin wires and the surfaces. The applied voltage may be a negative voltage of about 1000 V to about 10,000 V so that the thin electrodes are negatively charged and the plates are positively charged. Due to the applied voltage, the thin electrodes serve as charging electrodes that generate a relatively strong electric field capable of ionizing airborne particles that come within close proximity, and the conductive surfaces serve as collection surfaces to which the ionized particles are attracted to and adhere through electrostatic attraction. Various physical arrangement of the electrodes and surfaces are possible. The thin electrodes may be arranged as an array of point electrodes or thin wires. The conductive surfaces may be configured as an array of tubes, a honeycomb arrangement, or a stacks of plates.

A UVC irradiation unit may comprise one or more enclosed chambers with an intake and an outflow configured to allow passage of air therethrough. Each chamber comprises one or more UVC sources that generate UVC radiation, so that air passing through the chamber is irradiated with the UVC radiation. The UVC radiation may be characterized by a wavelength of between 100 nanometers (nm) and 280 nm, and a wattage of between 10 Watts (W) and 50 W.

An activated carbon filtration unit may comprise a bed of activated carbon through which an airflow is made to traverse. Activated carbon is typically made from charcoal that has been heat-treated, which creates a lattice of microscopic pores, thus resulting in a high surface area to volume ratio. Many gases and volatile compounds that pass through the activated carbon become adsorbed to the carbon surface, thus purifying the air made to traverse the carbon bed.

An $O_2$ ionization unit (or "$O_2$ ionizer") as used herein refers to an ionization device that is configured to ionize oxygen gas to preferentially produce $O_2-$ and $O_2+$ ions from ambient air.

An aerosol source is a device configured to introduce an aerosolized liquid into the airstream being conveyed through the ABA system. The liquid may comprise one or a combination of two or more of the following selections: a probiotic solution, a scent, or an odor absorber.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the invention in a figure may be used to reference the given feature. Dimensions of features shown in the figures are chosen for convenience and clarity of presentation and are not necessarily shown to scale.

FIG. 1 shows a chart listing various configurations of ABA reduction systems in accordance with an embodiment of the disclosure;

DETAILED DESCRIPTION

Figure 2:
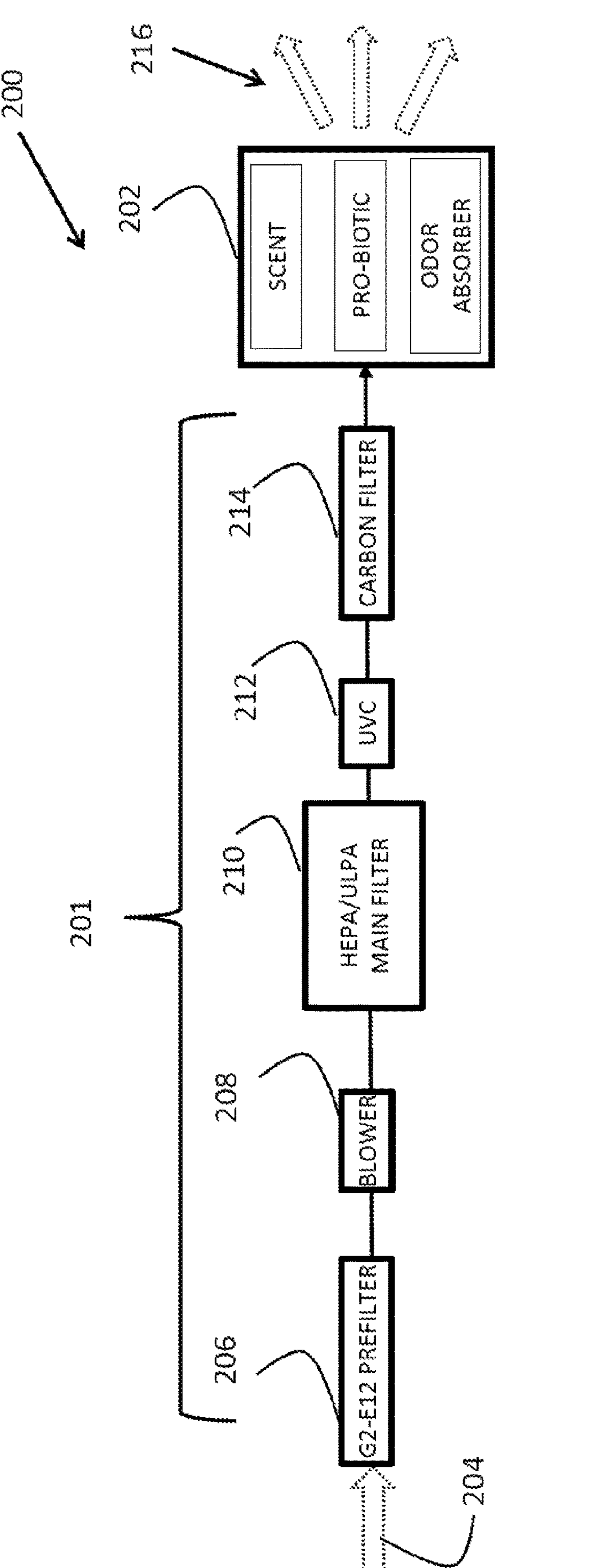
FIG. 2 shows a block diagram of an example ABA reduction system comprising a particulate filtration unit, which may be a HEPA filter or a ULPA filter, a UVC irradiation unit, an activated carbon filtration unit, and an aerosol source, in accordance with an embodiment of the disclosure.

FIG. 1 shows Chart 1, which provides various example configurations of ABA reduction systems in accordance with an embodiment of the disclosure.

Components of ABA reduction systems may be described herein with respect to an order of airflow, starting with an air intake and ending with an air exhaust, which may be recirculated into a room from which the air was initially received. As used herein, in a case where a first treatment unit is situated upstream of the airflow to receive the air being treated prior to a downstream second treatment unit, the first treatment unit may be described as being situated "before" the second treatment unit, and the second treatment unit may be described as being situated "after" the first treatment unit.

An ABA reduction system may comprise a combination of two or more of the following air treatment units: a UVC irradiation unit; an $O_2$ ionizer; an ESP unit; an activated carbon filtration unit. The ABA reduction system may comprise a blower and an appropriate arrangement of airflow conduits to propel and direct air through the two or more air treatment units in series.

The ABA reduction system may further comprise one or more particulate filtration units. Examples of particulate filtration units include high-efficiency particulate absorbing (HEPA) filter units, Ultra-Low Particulate Air (ULPA) filter units, and various types of pre-filters. HEPA filters are 99.97% effective for eliminating particulate matter of 0.3-micron diameter or larger. ULPA filters are 99.999% effective at removing submicron particulate matter of 0.12-micron diameter or larger. Examples of pre-filters include G2 pre-filters, G3 pre-filters, G4 pre-filters, M5 pre-filters, M6 pre-filters, F7 pre-filters, F8 pre-filters, F9 pre-filters, E10 pre-filters, E11 pre-filters, and E12 pre-filters.

In an embodiment of the disclosure, an ABA reduction system may be a UVC+Ionizer system configured to propel air to traverse, in order of airflow, a UVC irradiation unit and an $O_2$ ionizer. Without being limited by theory, both the UVC irradiation unit and the $O_2$ ionizer serve as virucidal units. The intensity of UVC irradiation and rate of airflow through the UVC irradiation unit may be configured for at least a predetermined percentage of virus comprised in a volume of treated air to be killed or inactivated during passage through the UVC irradiation unit. The predetermined percentage may be at least 90%, at least 95%, at least 99%, at least 99.9% or at least 99.99%. The UVC radiation may be characterized by a wavelength of between 100 nanometers (nm) and 280 nm, and a wattage of between 10 Watts (W) and 50 W. The $O_2$ ionizer may be configured to generate a sufficiently high concentration of $O_2-$ and $O_2+$ so that at least a predetermined percentage of virus comprised in a volume of treat air is killed or inactivated during passage through the $O_2$ ionizer. The predetermined percentage may be at least 90%, at least 95%, at least 99%, at least 99.9% or at least 99.99%. Without being bound by theory, the ionized $O_2$ generated by the $O_2$ ionizer may react with ambient water molecules in the air or present in the VCAPs to generate $H_2O_2$, which is a known virucidal agent. By way of example, the $O_2$ ionizer may be a Sterionizer™ disinfection unit (Filt Air Ltd.).

Optionally, the UVC+Ionizer system comprises a carbon filter situated after the UVC irradiation unit and before the $O_2$ ionizer. Optionally, the UVC+Ionizer system comprises one or more particulate filtration units situated before the UVC irradiation unit.

As shown in FIG. 1, an example UVC+Ionizer system may be configured as shown in Option A that comprises the following in order of airflow: a_prefilter, a blower, a UVC irradiation unit, and an $O_2$ ionizer.

Another example UVC+Ionizer system may be configured as shown in Option B that comprises the following in order of airflow: a prefilter, a HEPA or ULPA main filter, a blower, a UVC irradiation unit, and an $O_2$ ionizer.

Another example UVC+Ionizer system may be configured as shown in Option C that comprises the following in order of airflow: a prefilter, a HEPA or ULPA main filter, a blower, a UVC irradiation unit, an activated carbon filtration unit, and an $O_2$ ionizer.

In an embodiment of the disclosure, an ABA reduction system may be an ESP-based system configured to direct air to traverse, in order of airflow, an ESP unit and an activated carbon filtration unit. Without being limited by theory, an ESP system may remove VCAPs from the air through negatively charged charging electrodes ionizing the VCAPs and the ionized VCAPs being collected by positively charged collection plates. While ESP units may be configured to minimize ozone generation, the application of high strength electric fields often result in the creation of some residual ozone, which is a known irritant. The downstream activated carbon filtration unit may advantageously absorb any residual ozone generated by the ESP unit. In an embodiment, the activated carbon may be formulated to be positively charged to attract, and promote adsorption, of VCAPs ionized in the upstream ESP unit.

Optionally, the ESP-based system comprises one or more particulate filtration units situated before the ESP unit. Optionally, the ESP-based system comprises a HEPA or ULPA main filter situated before the ESP unit, and optionally a prefilter situated before the HEPA or ULPA main filter unit. Optionally, the EPS-based system comprises the prefilter but not the HEPA or ULPA main filter. Optionally, the ESP-based system comprises a UVC irradiation unit after the one or more particulate filtration units and before the ESP unit.

As shown in FIG. 1, an example ESP-based system may be configured as shown in Option D that comprises the following in order of airflow: a prefilter, a blower, and ESP unit, and an activated carbon filtration unit.

Another example ESP-based system may be configured as shown in Option E that comprises the following in order of airflow: a prefilter, a HEPA or ULPA main filter, a blower, an ESP unit, and an activated carbon filtration unit.

Another example ESP-based system may be configured as shown in Option F that comprises the following in order of airflow: a prefilter, a HEPA or ULPA main filter, a blower, a UVC irradiation unit, an ESP unit, and an activated carbon filtration unit.

In an embodiment of the disclosure, an ABA reduction system may be a combined system configured to direct air to traverse, in order of airflow, an ESP unit and an $O_2$ ionizer.

Optionally, the combination system comprises one or more particulate filtration units situated before the ESP unit. Optionally, the combination system comprises a HEPA or ULPA main filter unit situated before the ESP unit, and optionally a prefilter situated before the HEPA or ULPA main filter unit. Optionally, the combination system comprises the prefilter but not the HEPA or ULPA main filter unit. Optionally, the combination system comprises a UVC irradiation unit before the ESP unit, and optionally after the HEPA or ULPA main filter unit in a case where the system comprises a HEPA or ULPA main filter unit. Optionally, the combination system comprises an activated carbon filtration unit after the ESP unit and before the $O_2$ ionizer. Advantageously, the removal of VCAPs by the upstream ESP unit, as well as optionally, the activated carbon filtration unit, reduces the concentration of ionized $O_2$ required to kill or inactivate the virus in the remaining aVCAPs.

As shown in FIG. 1, an example combination system may be configured as shown in Option G that comprises the following in order of airflow: a prefilter, a HEPA or ULPA main filter unit, a blower, a UVC irradiation unit, an ESP unit, an activated carbon filtration unit, and an $O_2$ ionizer.

In an embodiment of the disclosure, an ABA reduction system may be a UVC+Carbon system configured to direct air to traverse, in order of airflow, a UVC irradiation unit and an activated carbon filtration unit. Optionally, the UVC+Carbon system comprises a prefilter situated before the UVC irradiation unit. Optionally, the UVC+Carbon system does not comprise a HEPA or ULPA main filter unit. Optionally, the UVC+Carbon system comprises a HEPA or ULPA main filter unit.

As shown in FIG. 1, an example UVC+Carbon system may be configured as shown in Option H that comprises the following in order of airflow: a prefilter, a blower, and UVC irradiation unit, and an activated carbon filtration unit. The UVC+Carbon system as shown in Option H may further include a HEPA or ULPA main filter unit.

As shown in FIG. 1, an ABA reduction system in accordance with an embodiment of the disclosure may further comprise an aerosol source. The aerosol source may be placed downstream of all air treatment units (filter and/or UVC units) comprised in the ABA reduction system so that the aerosol is efficiently released with purified air output 216 into the room serviced by the ABA reduction system, without being captured, blocked, or degraded by any of the air treatment units.

The aerosol source is configured to hold a conditioning liquid and release the conditioning liquid as an aerosol at a predetermined rate into the air output of the ABA reduction system. The releasing mechanism of the aerosol source may be controlled in coordination with the blower to maintain a relatively constant aerosol concentration in the air output through changes in the air conveyance rate of the ABA reduction system.

The conditioning liquid may comprise one or a combination of two or more of the following: a probiotic solution, a scent solution, and an odor absorber solution.

The probiotic solution may comprise nonpathogenic bacteria, by way of example *Bacillus* species, such as *Bacillus coagulans, Bacillus lentus, Bacillus lichenijormis*, or *Bacillus pumilus*. The probiotic solution, when released as an aerosol into the output air of the ABA reduction system, settles on surfaces in a room serviced by the ABA reduction system. Once on the surface, the non-pathogenic bacteria grow and consume nutritional resources present on the surface, thus preventing growth of other micro-organisms (such as bacteria or mold) that may be harmful to humans. An ABA reduction system having an aerosol source releasing aerosolized probiotic solution combines, in one system, air purification with probiotic treatment of room surfaces. Releasing aerosolized probiotic solution with a purified air output from the ABA reduction system results in introducing non-pathogenic micro-organisms to room surfaces while simultaneously preventing or minimizing the introduction of new pathogenic micro-organisms on the same surfaces, thus advantageously increasing the efficiency and/or speed by which the probiotic treatment reduces the concentration of pathogenic micro-organisms on the treated surfaces.

The scent solution may comprise volatile compounds that are generally found pleasing, so that an ABA reduction system maintains a pleasing odor in a room. Various volatile compounds characterized by pleasing smell are known in the art. The odor absorber solution may comprise odor absorbing compounds that bind to or degrade malodorous compounds. By removing or degrading other odorous compounds prior to the addition of the aerosolized scent solution and/or the odor absorber solution, the ABA reduction system advantageously allows for substantially less aerosolized scent solution and/or the odor absorber solution to be required to improve the scent of a room being serviced by the system. In addition, combining non-pathogenic micro-organisms with a scent in the conditioning solution advantageously provides for a user of the ABA reduction system to be able to readily perceive when the non-pathogenic micro-organisms have been released with purified air output 216.

Reference is made to FIG. 2, which shows, as a block diagram, an example ABA reduction system 200 as shown in Option H (UVC+Carbon) of FIG. 1, comprising a HEPA or ULPA filter unit and an aerosol source.

ABA reduction system 200 comprises a air purification stack 201 configured take in air input 204 through an air intake (not shown), convey the air with a blower 208 through a series of air treatment units to remove and/or degrade unwanted particles and compounds, introduce using an aerosol source 202 a conditioning liquid in aerosol form into the air purified by air purification stack 201, and blow out a purified air output 216. Air input 204 may be air from a designated indoor space serviced by the ABA reduction system. The ABA reduction system may be connected to or integrated within an HVAC system. The ABA reduction system may be configured through an arrangement of air ducts to service a plurality of indoor spaces. By way of example, the ABA reduction system may be connected to or integrated with a central HVAC system. Alternatively, the ABA reduction system may be configured as standalone device.

The air treatment units as shown in FIG. 2A comprises, in upstream to downstream order, a prefilter 206, a main particulate filter 210 that may comprise a HEPA or an ULPA filter, a UVC irradiation unit 212 and an activated carbon filter 214.

Figures 3A, 3B, 3C:
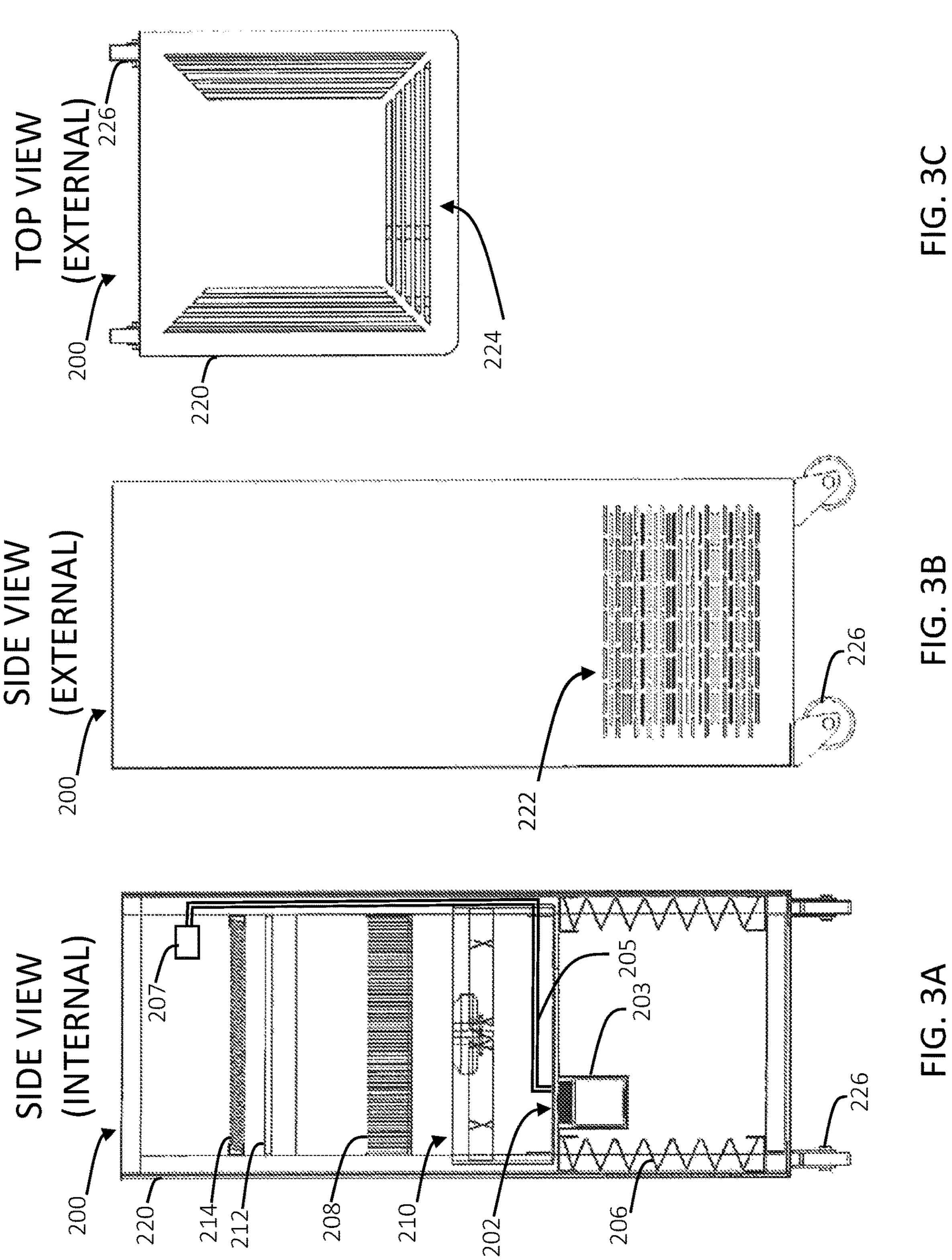
FIGS. 3A-3C schematically shows an example ABA reduction system in accordance with an embodiment of the disclosure.

FIGS. 3A-3C schematically shows an embodiment of B-Pure system 200 as a mobile, standalone device. For convenience of presentation, the standalone, mobile embodiment of ABA reduction system 200 shown in FIGS. 3A-3C may be referred to herein as a "B-pure system". FIG. 3A shows a side interior view of the B-pure system showing prefilter 206, main particulate filter 210 (in this embodiment a ULPA filter), a blower 208, UVC irradiation unit 212, activated carbon filter 214, and aerosol source 202 housed inside a metal frame 220. As shown in FIG. 3A, aerosol source 202 may comprise a liquid reservoir 203 and a dispensing tube 205 that carries the liquid from the liquid reservoir to a region downstream activation carbon filter 214, for aerosolization and release through an aerosolization mechanism 207. B-Pure system 200 further comprises air intake vents 212 (shown in FIG. 3B) on a side surface of the metal frame, air outflow vents 214 (shown in FIG. 3C) on a top surface of the metal frame, and wheels 226. With the wheels, B-Pure system 200 may be moved from one room to another as needed.

Table 1 shows functional and physical parameters of the B-pure system shown in FIGS. 3A-3C.

TABLE 1

| Parameter | |
|---|---|
| Airflow | Adjustable up to 500 m^3/hr |
| Filtration efficiency | 99.9995% for particles having diameter of 0.1 microns to 0.2 microns |
| UV source | 254 nm wavelength; 24 W |
| dimensions | 50 cm length × 50 cm width × 50 cm height |

Figure 4B:
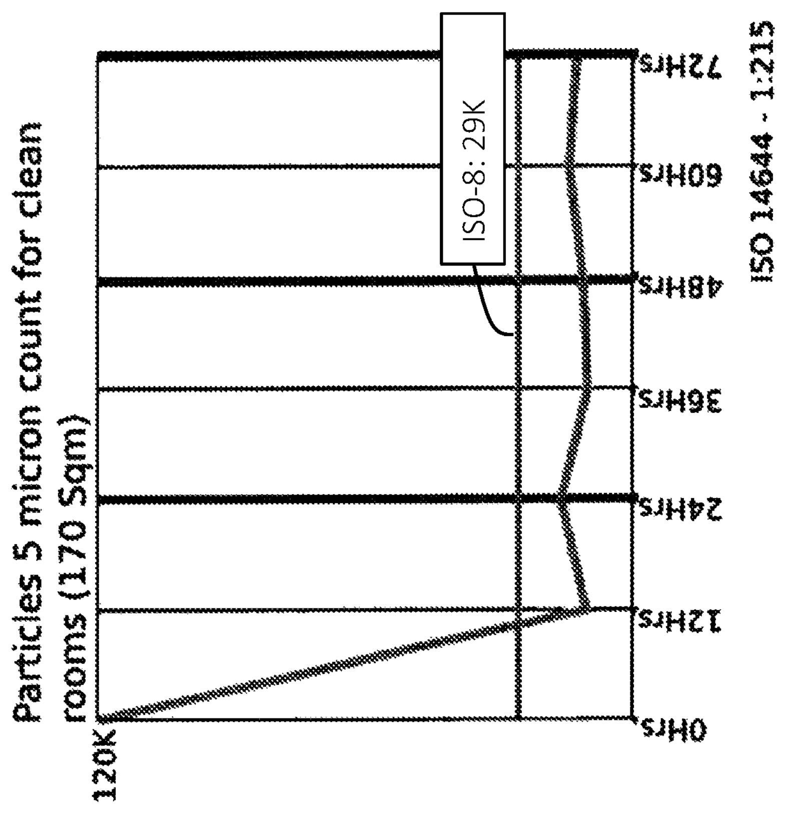
FIGS. 4A-4C shows results of parametric tests of the example ABA reduction system shown in FIGS. 3A-3B.
Figure 4A:
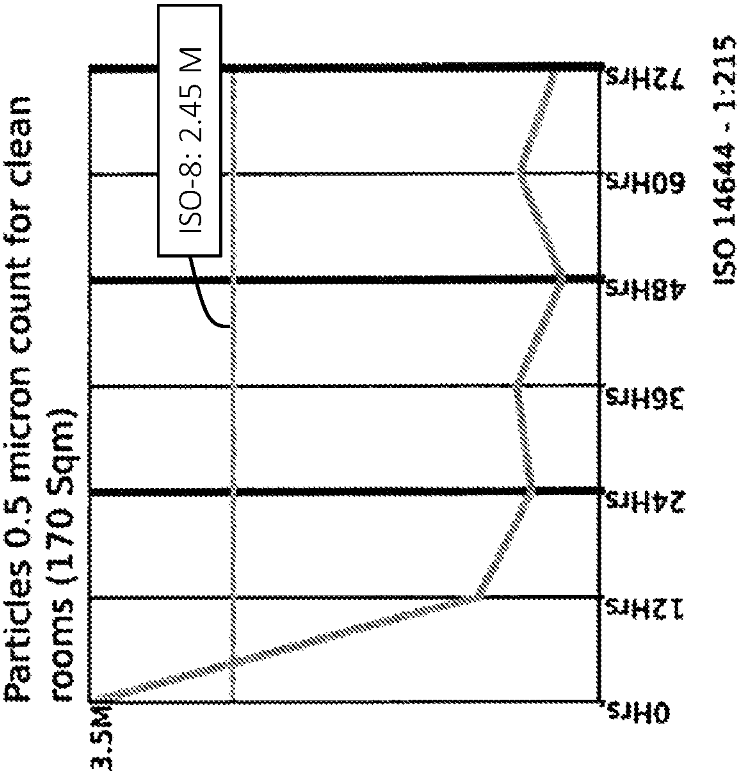
Figure 4C:
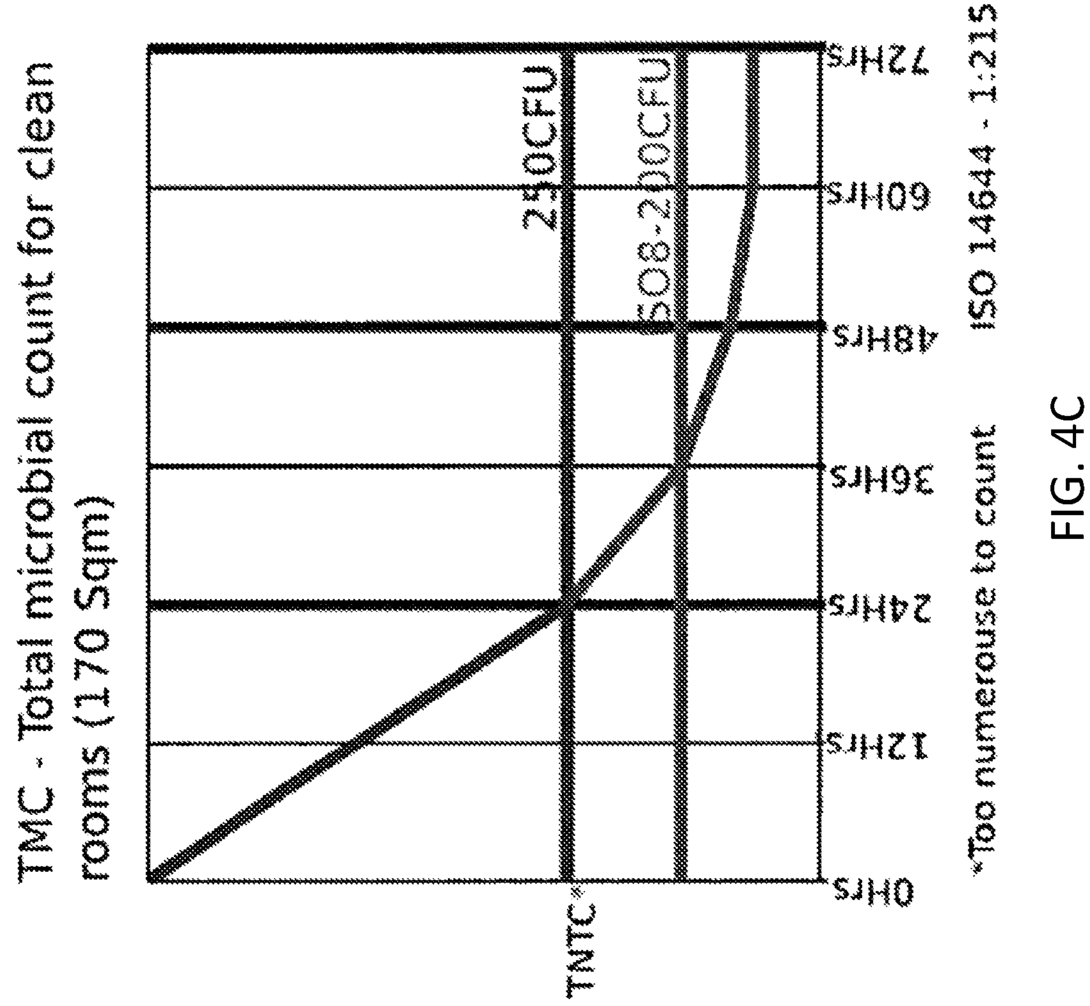

FIGS. 4A-4C shows results from functional tests of the B-Pure system. In test rooms having a total air volume of 170 square meters (m^2), the B-Pure system was found to reduce 0.5 micron diameter particles (FIG. 4A) and 5 micron diameter particles (FIG. 4B) to well below the requirement of cleanroom classification ISO-8 within 12 hours, and to reduce total microbial count (TMC; FIG. 4C) to the requirement of cleanroom classification ISO-8 within 36 hours.

Virus inactivation efficacy of the B-pure system was also tested. An *Escherichia* phage MS2 solution with a defined concentration was sprayed as a bioaerosol. The phage-enriched air was allowed to pass through the B-Pure system at an airflow of 250 m^3/hr, and the outflowing air was passed through an absolute filter to collect any remaining viable phage particles. The concentration of viable phage particles collected from the absolute filter was determined by counting PFU (plaque forming unit) in a bed of *E. coli* using a double agar layer method after 24 h of incubation at 37±1° C. The test was run under two conditions: an experimental condition with the B-Pure system running normally, and a control condition in which ULPA filter 210 was removed and UVC unit 202 was inactive. Virus disinfection efficacy was calculated as a percentage using the following formula:

$$(1-(\text{experimental PFU}/\text{control PFU}))*100$$

Based on the above conditions, it was found that one pass of the virus-infused air through the B-Pure system achieved a virus disinfection efficacy of 91.7%. If the same treated air was recycled through the B-Pure system again as a second pass, the virus disinfection efficacy is expected to be 99.3%. After a third pass, the virus disinfection efficacy is expected to be 99.95%. It will be appreciated that when the B-Pure system is used to treat the air within and enclosed room with little to no air exchange, the air in the room will be conveyed through the B-Pure system in multiple passes, so that the virus disinfection efficacy will exceed 91.7%. By way of example, In a room where the B-Pure system is configured to perform three air changes in an hour, the virus disinfection efficacy of the B-Pure system will be 99.5% at one hour of use.

As note herein above, aerosolized probiotic solution with a purified air output from an ABA reduction system results advantageously increasing the efficiency and/or speed by which the probiotic treatment reduces the concentration of pathogenic micro-organisms on the treated surfaces. It is well known that surfaces (such as table, desk, chair surfaces) that are cleaned with chemical detergents on a regular basis can nevertheless maintain a steady population of pathogenic mold and bacteria. In a control probiotic treatment, a mix of non-pathogenic *Bacillus* species was released into the air output of a standard central HVAC system with no air-purification beyond a pre-filter (that is, no HEPA or ULPA filter, no activated carbon filter, and no UVC treatment), which serviced a dental office. Over a 36 day trial, it was found that the probiotic treatment resulted in an elimination of endemic pathogenic bacteria measured as a % reduction in colony forming units (CFUs) in samples gathered from test surfaces) after 17 days. The same treatment resulted in elimination of mold (also measured as % reduction in CFUs) after 36 days. When the office is treated with an experimental treatment with the B-Pure system, in which the probiotic aerosol is dispersed with air that has been purified through UPLA filtration, UVC treatment, and activated carbon filtration, it is found that the elimination of surface mold and pathogenic bacteria is achieved at an earlier time point compared to the control probiotic treatment.

There is therefore provided an air treatment system comprising: an air purification assembly comprising one or more air purification modules and configured to, in an upstream to downstream order, take in air, produce purified air by conveying the air to traverse the one or more air purification modules, and expel the purified air; and an aerosol source configured to release a conditioning liquid in aerosol form into the purified air.

In an embodiment of the disclosure, the conditioning liquid comprises a predetermined concentration of non-pathogenic micro-organisms. Optionally, the conditioning liquid comprises a scent. Optionally, the conditioning liquid comprises an odor absorbing compound.

In an embodiment of the disclosure, the one or more air purification modules comprises, in an upstream to downstream order, a HEPA or ULPA filter, a UVC irradiation unit, and an activated carbon filter. Optionally, the HEPA or ULPA filter is a ULPA filter. Optionally, the UVC irradiation unit is configured to generate UVC irradiation characterized by a wavelength of between 100 nm and 280 nm. Optionally, the UVC irradiation is characterized by a wattage of between 10 W and 50 W.

There is also provided an air treatment system comprising: an air purification assembly comprising one or more air purification modules and configured to, in an upstream to downstream order, take in air, produce purified air by conveying the air to traverse the one or more air purification modules, and expel the purified air, wherein the one or more air purification modules comprises a ULPA filter, a UVC irradiation unit, and an activated carbon filter arranged in an upstream to downstream arrangement. Optionally, the air treatment system further comprising an aerosol source configured to release a predetermined concentration of non-pathogenic micro-organisms in aerosol form into the purified air. Optionally, the UVC irradiation unit is configured to generate UVC irradiation characterized by a wavelength of between 100 nm and 280 nm. Optionally, the UVC irradiation is characterized by a wattage of between 10 W and 50 W.

There is also provided a method of reducing pathogenic micro-organisms present on surfaces of a room, the method comprising: dispensing, into the room, purified air that has been purified with an air purification system; and dispensing a probiotic solution in aerosol form into the purified air so that it will be dispensed into the room with the purified air, wherein the probiotic solution comprises non-pathogenic bacteria. Optionally, the probiotic solution comprises a scent. Optionally, the probiotic solution comprises an odor absorbing compound.

In an embodiment of the disclosure, the air purification system comprises, in an upstream to downstream order, a HEPA or ULPA filter, a UVC irradiation unit, and an activated carbon filter. Optionally, the HEPA or ULPA filter is a ULPA filter. Optionally, the UVC irradiation unit is configured to generate UVC irradiation characterized by a wavelength of between 100 nm and 280 nm.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. An air treatment system comprising:

an air purification assembly comprising one or more air purification modules in an upstream to downstream order, an air intake, a prefilter, a blower operable to flow air through the purification assembly at 250 $m^3$/hr, an Ultra-Low Particulate Air filter (ULPA) or a High-Efficiency Particulate Absorbing (HEPA) filter having filtration efficiency at 99.9995% for particles of diameter between 0.1-0.2 micron, a short-wavelength Ultraviolet (UVC) Irradiation unit operable at 24 W (watts) to produce UV light at 254 nm wavelength, and a carbon filter; and an aerosol source configured to release a conditioning liquid in aerosol form into the purified air, wherein when operating in a 170 square meters (m2) test room, at the stated operatable values and the blower operating to flow air through the purification system at 250 $m^3$/hr, within 12 hours the system reduces 0.5 micron diameter particles from a concentration of about $3.5\times10^6$ particles per $m^3$ to less than about a third of the ISO-8 clean room standard of $2.45\times10^6$ particles/$m^3$ and 5 micron diameter particles from a concentration of about $120\times10^3$ particles per $m^3$ to less than about a half of the ISO-8 clean room standard of $29\times10^3$ particles/$m^3$.

2. The air treatment system according to claim 1, wherein the conditioning liquid comprises a predetermined concentration of nonpathogenic micro-organisms.

3. The air treatment system according to claim 2, wherein the conditioning liquid comprises a scent.

4. The air treatment system according to claim 2, wherein the conditioning liquid comprises an odor absorbing compound.

5. The air treatment system according to claim 1, wherein the UVC irradiation unit is configured to generate UVC irradiation characterized by a wavelength of between 100 nm and 280 nm.

6. The air treatment system according to claim 1, wherein the UVC irradiation is characterized by a wattage of between 10 W and 50 W.

* * * * *